United States Patent
Squires et al.

(10) Patent No.: US 10,231,849 B2
(45) Date of Patent: Mar. 19, 2019

(54) SURGICAL INSTRUMENT SYSTEM AND METHOD

(71) Applicant: Warsaw Orthopedic, Inc., Warsaw, IN (US)

(72) Inventors: Craig M. Squires, Cordova, TN (US); Steven S. Gill, Clifton Bristol (GB); Joshua A. Ruth, Edina, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/293,042

(22) Filed: Oct. 13, 2016

(65) Prior Publication Data
US 2018/0104072 A1  Apr. 19, 2018

(51) Int. Cl.
| | |
|---|---|
| *A61F 2/46* | (2006.01) |
| *A61B 90/00* | (2016.01) |
| *A61B 17/16* | (2006.01) |
| *A61B 17/17* | (2006.01) |
| *A61B 17/70* | (2006.01) |
| *A61F 2/44* | (2006.01) |
| *A61B 17/00* | (2006.01) |

(52) U.S. Cl.
CPC ........ *A61F 2/4611* (2013.01); *A61B 17/1671* (2013.01); *A61B 17/1757* (2013.01); *A61B 17/7074* (2013.01); *A61B 90/39* (2016.02); *A61F 2/442* (2013.01); *A61F 2/4684* (2013.01); *A61B 2017/00261* (2013.01); *A61B 2017/00477* (2013.01); *A61B 2090/034* (2016.02)

(58) Field of Classification Search
CPC .................................................... A61F 2/4611
See application file for complete search history.

(56) References Cited

U.S. PATENT DOCUMENTS

| | | | |
|---|---|---|---|
| 5,676,701 A | 10/1997 | Yuan et al. | |
| 5,913,860 A | 6/1999 | Scholl | |
| 6,113,637 A | 9/2000 | Gill et al. | |
| 6,228,118 B1 | 5/2001 | Gordon | |
| 6,319,257 B1 | 11/2001 | Cariganan et al. | |
| 6,540,785 B1 | 4/2003 | Gill et al. | |
| 7,276,082 B2 | 10/2007 | Zdeblick et al. | |
| 7,491,204 B2 | 2/2009 | Marnay et al. | |
| 7,655,012 B2 | 2/2010 | DiPoto et al. | |
| 7,655,045 B2 | 2/2010 | Richelsoph | |
| 7,666,186 B2 | 2/2010 | Harp | |
| 7,670,377 B2 | 3/2010 | Zucherman et al. | |
| 7,691,146 B2 | 4/2010 | Zucherman et al. | |
| 7,713,304 B2 | 5/2010 | Ankney | |
| 7,780,676 B2 | 8/2010 | Lakin et al. | |
| 7,794,465 B2 | 9/2010 | Marik et al. | |
| 7,799,083 B2 | 9/2010 | Smith et al. | |
| 7,806,932 B2 | 10/2010 | Webb et al. | |
| 7,828,847 B2 | 11/2010 | Abdou | |
| 7,842,088 B2 | 11/2010 | Rashbaum et al. | |
| 7,846,210 B2 | 12/2010 | Pere-Cruet et al. | |
| 7,892,262 B2 | 2/2011 | Rhoda et al. | |
| 7,896,884 B2 | 3/2011 | Wing et al. | |

(Continued)

*Primary Examiner* — Nicholas J Plionis

(57) ABSTRACT

A surgical instrument includes a trial including a mating element. A member has a tissue engagement surface and a mating part releasably engageable with the mating element such that the trial is interchangeable with a plurality of alternate members. Systems, implants and methods are described.

20 Claims, 14 Drawing Sheets

(56) References Cited

U.S. PATENT DOCUMENTS

| | | | |
|---|---|---|---|
| 7,909,877 B2 | 3/2011 | Krueger et al. | |
| 7,947,044 B2 | 3/2011 | Ullrich, Jr. et al. | |
| 8,021,427 B2 | 9/2011 | Spoonamore | |
| 8,038,716 B2 | 10/2011 | Duggal et al. | |
| 8,092,539 B2 | 1/2012 | Ralph et al. | |
| 8,337,500 B2 | 12/2012 | Bertagnoli et al. | |
| 8,419,742 B2 | 4/2013 | Marnay et al. | |
| 8,562,682 B2 | 10/2013 | Gill et al. | |
| 8,663,229 B2 | 3/2014 | Marnay et al. | |
| 2004/0059271 A1* | 3/2004 | Berry | A61F 2/44 602/32 |
| 2004/0215198 A1* | 10/2004 | Marnay | A61B 17/1604 606/86 R |
| 2005/0027300 A1* | 2/2005 | Hawkins | A61B 17/025 606/86 R |
| 2005/0055029 A1 | 3/2005 | Marik et al. | |
| 2006/0217807 A1* | 9/2006 | Peterman | A61F 2/4455 623/17.11 |
| 2008/0269756 A1* | 10/2008 | Tomko | A61B 17/1757 606/87 |
| 2008/0275455 A1* | 11/2008 | Berry | A61F 2/4611 606/99 |
| 2009/0276051 A1* | 11/2009 | Arramon | A61F 2/4425 623/17.16 |
| 2010/0217395 A1 | 8/2010 | Bertagnoli et al. | |
| 2010/0292800 A1* | 11/2010 | Zubok | A61B 17/1604 623/17.16 |
| 2010/0298941 A1* | 11/2010 | Hes | A61F 2/4425 623/17.16 |
| 2011/0060859 A1 | 3/2011 | Shukla et al. | |
| 2011/0077739 A1 | 3/2011 | Rashbaum et al. | |
| 2011/0082553 A1 | 4/2011 | Abdou | |
| 2011/0082556 A1 | 4/2011 | Duggal et al. | |
| 2011/0092976 A1 | 4/2011 | Rawles et al. | |
| 2011/0178600 A1 | 7/2011 | Moskowitz et al. | |
| 2012/0271312 A1* | 10/2012 | Jansen | A61B 17/1604 606/80 |
| 2014/0172105 A1* | 6/2014 | Frasier | A61F 2/4611 623/17.16 |
| 2015/0272650 A1* | 10/2015 | Dubois | A61F 2/4611 606/99 |

\* cited by examiner

SURGICAL INSTRUMENT SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy, implantable prosthetics and arthroplasty. For example, surgical instruments are employed to prepare tissue surfaces for disposal of implants. In some cases, all or a portion of an intervertebral disc is replaced and surgical treatment can include disc arthroplasty. This surgical treatment includes insertion of an artificial intervertebral disc implant into an intervertebral space between adjacent vertebrae. Surgical instruments are also employed to engage the implant for disposal with the tissue surfaces at a surgical site. Such implants can restore the mechanical support function of vertebrae and provide relative movement of the adjacent vertebrae. This disclosure describes an improvement over these prior technologies.

SUMMARY

In one embodiment, a surgical instrument is provided. The surgical instrument includes a trial including a mating element. A member has a tissue engagement surface and a mating part releasably engageable with the mating element such that the trial is interchangeable with a plurality of alternate members. In some embodiments, systems, implants and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
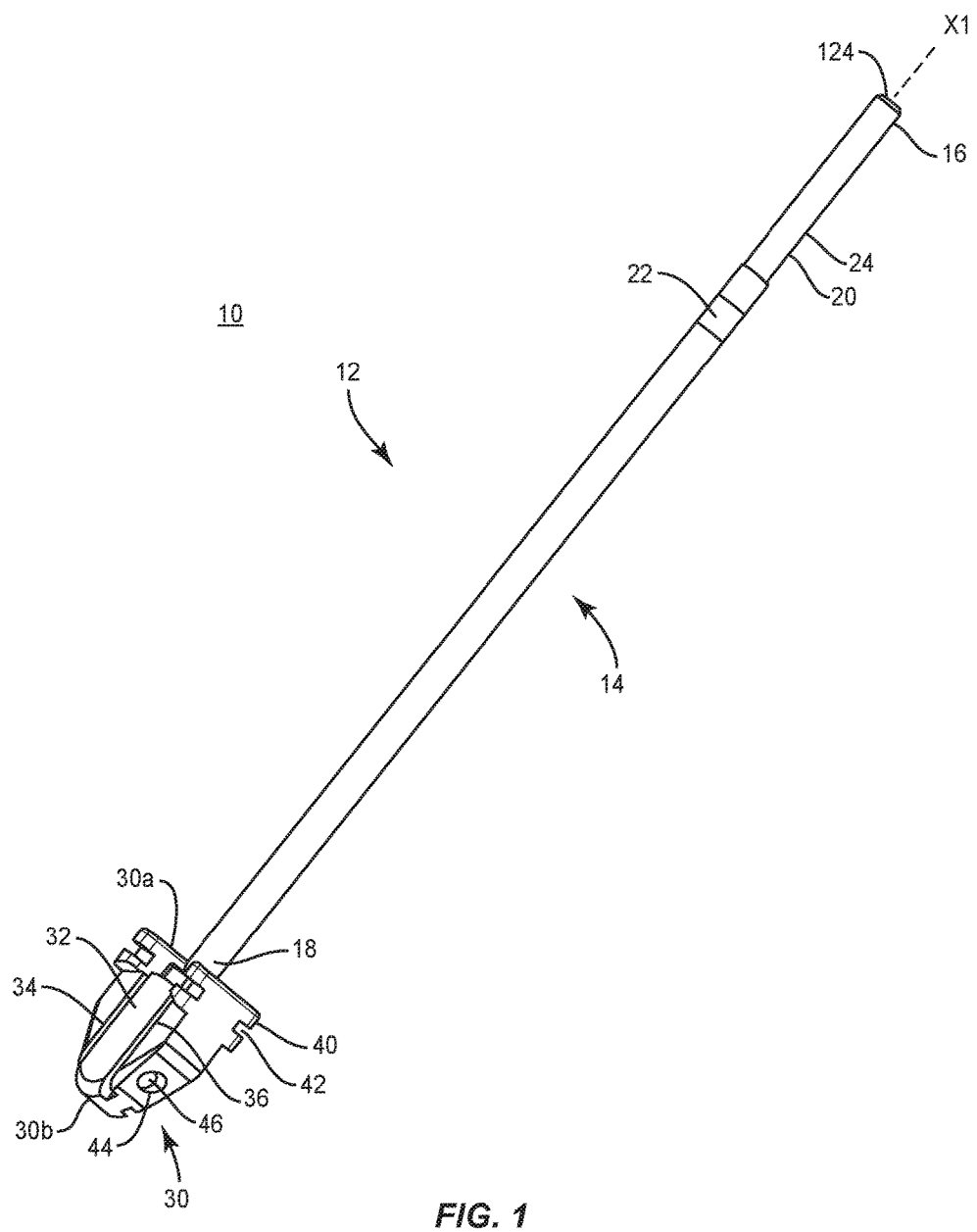
FIG. 1 is a perspective view of components of one embodiment of a surgical system in accordance with the principles of the present disclosure.
Figure 2:
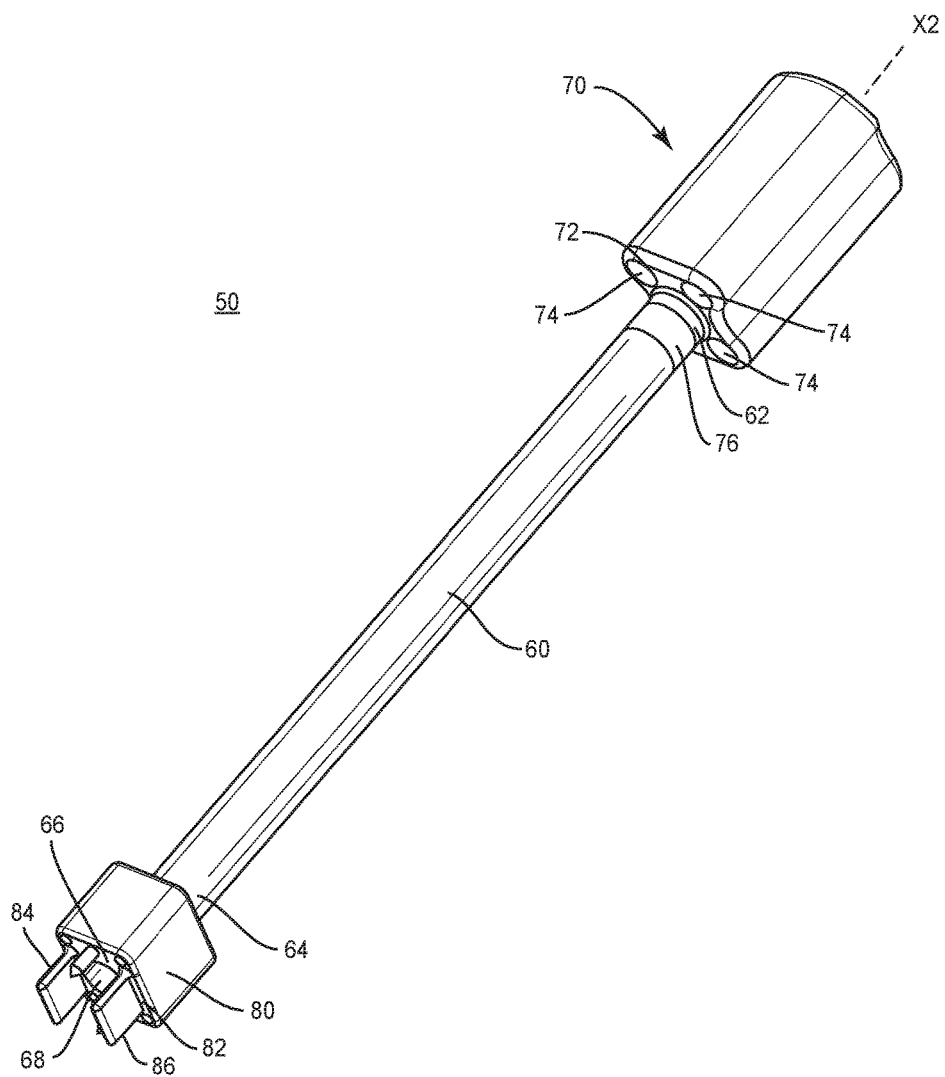
FIG. 2 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system for treating a spine at a surgical site and a method for treating a spine. In some embodiments, the systems and methods of the present disclosure are employed with a spinal joint and fusion, for example, with a cervical, thoracic, lumbar and/or sacral region of a spine.

In some embodiments, the present system includes a surgical instrument, such as, for example, a trial configured to streamline instrumentation use and connection with other surgical instruments. In some embodiments, the other surgical instruments include, such as, for example, a cutter guide and a rail punch. In some embodiments, the trial includes a shaft having a knurled gripping end. In some embodiments, the trial includes a colored indicator, such as, for example, a band configured to indicate a size of the trial. In some embodiments, the trial includes a mating element, such as, for example, slots. In some embodiments, the slots are configured for a mating engagement with a portion of the cutter guide and the rail punch. In some embodiments, the trial includes transverse slots configured to verify seating orientation of the cutter guide, such as, for example, a not fully seated position where the transverse slots are viewable and a fully seated position were the slots are obscured. In some embodiments, the trial includes an opening configured to verify that the trial is properly positioned and determine a verification marker position.

In some embodiments, the cutter guide includes a color band configured to match the color band of the trial. In some embodiments, the cutter guide includes mating elements, such as, for example, fins configured to mate with the slots. In some embodiments, the cutter guide includes a top pin configured to engage the drill guide with a top vertebral body and a bottom pin configured to engage the drill guide with a bottom vertebral body. In some embodiments, the pins are configured to facilitate stability.

In some embodiments, the rail punch includes a color band configured to match the color band of the trial. In some embodiments, the rail punch includes an end having a reduced cross section and an opening. In some embodiments, the knurled surface of the shaft of the trial is configured for access through the opening to facilitate simultaneous manipulation of the trial and the rail punch. In some embodiments, the rail punch includes mating elements, such as, fins configured for engagement with the slots. In some embodiments, the rail punch includes a depth stop. In some embodiments, the rail punch includes a shaft configured for disposal relative to the trial between a not fully seated position and a fully seated position.

In some embodiments, the trial is utilized with a surgical procedure including the steps of inserting the trial into a vertebral space and maintaining the trial within the vertebral space for all steps of the procedure. In some embodiments, the method includes the step of assembling the trial with a rail cutting instrument. In some embodiments, after the rail cutting instrument is utilized, a rail punch is assembled with the trial. In some embodiments, the trial and rail punch are moved by being grasped together simultaneously and removed together.

In some embodiments, proximal ends of the trial and the rail punch are flush when the punch is complete. In some embodiments, radiographic features are disposed on the trial and/or the drill guide to provide a visual confirmation of positioning.

In some embodiments, the surgical instrument is configured to facilitate insertion of instruments into the vertebral disc space. In some embodiments, the trial is configured to remain within the vertebral space during distraction and decompression preventing the vertebral disc space from collapsing.

In some embodiments, the trial is configured to remain in the vertebral disc space during the procedure. In some embodiments, the surgical instruments are cannulated and configured to translate over the trial shaft. In some embodiments, the surgical instrument is configured to engage the anatomy without having to re-elevate, and re-orient the vertebral bodies simultaneously. In some embodiments, the drill guide includes spikes configured to engage each vertebral body, and therefore secure the position of the surgical instrument during the procedure.

In some embodiments, the rail punches are height specific, so that instead of having one of each for every implant size the surgical system has only one of each for each implant height. In some embodiments, the surgical system eliminates the need for use of temporary fixation pins. In some embodiments, the surgical system reduces the number of instruments required for each set. In some embodiments, the surgical system eliminates the need for the titanium handles. In some embodiments, the surgical system provides instruments made as a single piece, rather than multi-piece assemblies, therefore reducing the cost of each instrument.

In some embodiments, the present system includes an automated surgical instrument configured to prepare an intervertebral disc space in connection with a surgical procedure. In some embodiments, the surgical instrument is employed with a method for treating a spine to remove tissue to facilitate creation of a cavity in the tissue at a surgical site to place mechanical and/or biologic materials in the cavity for a fusion across an intervertebral disc space. In some embodiments, the surgical instrument includes a hand-held instrument. In some embodiments, the present system and methods avoid the repetitive nature of disc space preparation that can lead to fatigue and inadequate removal of tissue and preparation of the intervertebral disc space. In some embodiments, the present system and methods avoid the hazards associated with surgery adjacent sensitive anatomy, such as, for example, nerve roots and/or the spinal cord.

In some embodiments, one or all of the components of the present system may be disposable, peel pack and/or pre packed sterile devices. One or all of the components of the system may be reusable. The system may be configured as a kit with multiple sized and configured components.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including surgical instruments, related components and methods of employing the surgical system. Alternate embodiments are also disclosed. Reference is made in detail to the exemplary embodiments of the present disclosure, which are illustrated in the accompanying figures. Turning to FIGS. 1-11, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a fully open surgical procedure, a minimally invasive procedure including percutaneous techniques, and mini-open surgical techniques. Surgical system 10 includes surgical instrumentation that can prepare tissue surfaces, and deliver and introduce a spinal implant at a surgical site of a patient. In some embodiments, the spinal implant can include one or more components of one or more spinal constructs, such as, for example, implantable prosthetics, cages, spacers, vertebral devices, bone fasteners, spinal rods, connectors and/or plates. In some embodiments, the components of surgical system 10 may be employed with a surgical treatment including disc arthroplasty, such as an anterior cervical arthroplasty, to restore the mechanical support function of vertebrae and provide relative movement of adjacent vertebrae. In some embodiments, the components of surgical system 10 can remove intervertebral disc tissue and insert an artificial intervertebral disc implant into an intervertebral space between adjacent vertebrae. In some embodiments, surgical system 10 may be employed with surgical procedures, for example, corpectomy, discectomy, fusion and/or fixation treatments that employ spinal implants to restore the mechanical support function of vertebrae.

Surgical system 10 includes a surgical instrument, such as, for example, a trial 12. Trial 12 includes a mating element, as described herein, for connection to a mating part of one or a plurality of members, such as, for example, surgical instruments in a configuration for treating one or multiple pathologies without removal of trial 12 from a surgical site, as described herein. Trial 12 is compatible and/or interchangeable with the plurality of alternate surgical instruments such that trial 12 can remain in an intervertebral disc space during surgical treatment, as described herein. In some embodiments, this configuration allows trial 12 to be interchangeable with one or a plurality of alternate surgical instruments such that the surgical instruments can engage tissue without the need to re-elevate and/or re-orient adjacent vertebrae simultaneously. This configuration can reduce instrumentation and cost of surgical treatment. In some embodiments, the alternate surgical instruments may comprise various surgical instruments, which may be provided and arranged as a kit.

Trial 12 includes a shaft, such as, for example, a handle 14 that extends between an end 16 and an end 18 along an axis X1. End 16 includes a surface 20 that includes a knurled surface 24 configured to facilitate manipulation of trial 12. In some embodiments, end 16 includes indicia, such as, for example, a band 22. In some embodiments, band 22 includes a color configured to indicate a dimension, such as, for example, a width and/or depth of trial 12.

End 18 includes a body 30 that extends between an end 30a and an end 30b. Body 30 is configured for disposal between vertebrae during a surgical procedure. Body 30 is configured to maintain a height between adjacent vertebrae and facilitate determination of a size of an implant 200 to be disposed with the vertebrae, as described herein. In some embodiments, a size of body 30 is configured to match a size and dimension of implant 200. Trial 12 measures a height between the vertebrae, depth and width such that implant 200 will fit snug between the vertebrae without further distraction.

Body 30 includes a surface 32 that defines a mating element, such as, for example, a slot 34 and a slot 36. Slot 34 and slot 36 are spaced apart and each extend axially along axis X1. In some embodiments, slot 34 extends in alternate orientations relative to axis X1, such as, for example, transverse, perpendicular and/or other angular orientations such as acute or obtuse. In some embodiments, slot 36 extends in alternate orientations relative to axis X1, such as, for example, transverse, perpendicular and/or other angular orientations such as acute or obtuse.

Slots 34, 36 are engageable with a mating part of one or a plurality of alternate surgical instruments. In some embodiments, trial 12 includes slot 34 and/or slot 36 for compatibility and/or interchangeability with alternate surgical instruments, such as, for example, a drill guide 50 and a rail punch 52, as described herein. In some embodiments, trial 12 is interchangeable with the alternate surgical instruments to facilitate maintaining body 30 between adjacent vertebrae while utilizing the alternate surgical instruments for engaging, cutting and/or otherwise treating tissue during a surgical procedure. In some embodiments, the mating element and the mating part, and/or trial 12 may be interchangeably connected with an alternate surgical instrument via friction fit, pressure fit, interlocking engagement, dovetail connection, hook and loop closure, clips, barbs, tongue in groove, threaded, magnetic, key/keyslot, drill chuck and/or adhesive.

Body 30 includes a surface 40 that defines slots 42, 42*a* disposed adjacent end 30*a*. Slots 42, 42*a* are disposed in a transverse orientation, such as, for example, a perpendicular orientation relative to axis X1. In some embodiments, slots 42, 42*a* extend in alternate orientations relative to axis X1, such as, for example, axial, perpendicular and/or other angular orientations such as acute or obtuse.

Figure 3:
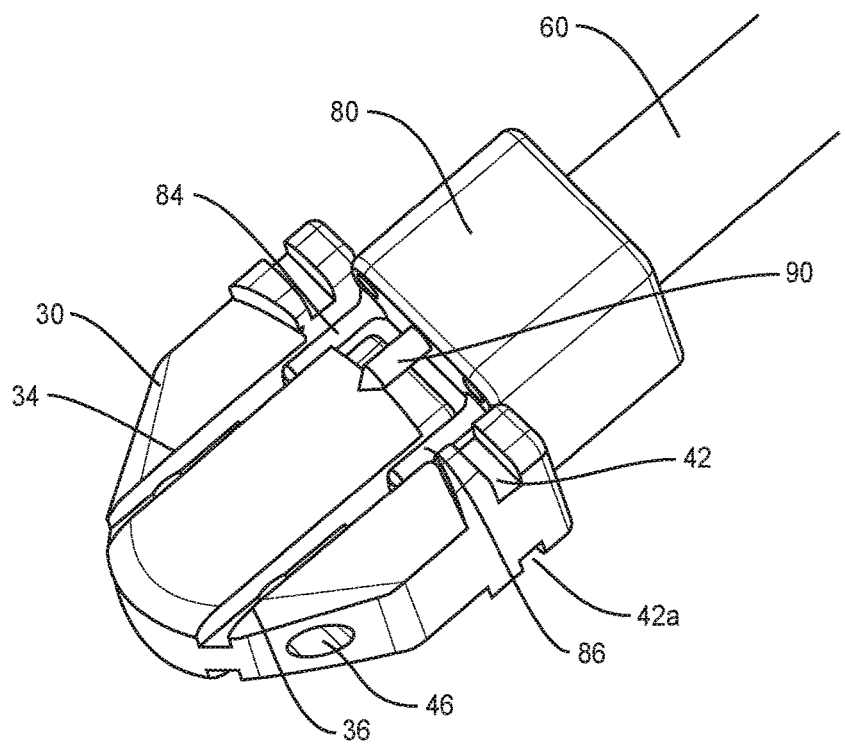
FIG. 3 is an enlarged break away view of components of one embodiment of a surgical system in accordance with the principles of the present disclosure.
Figure 4:
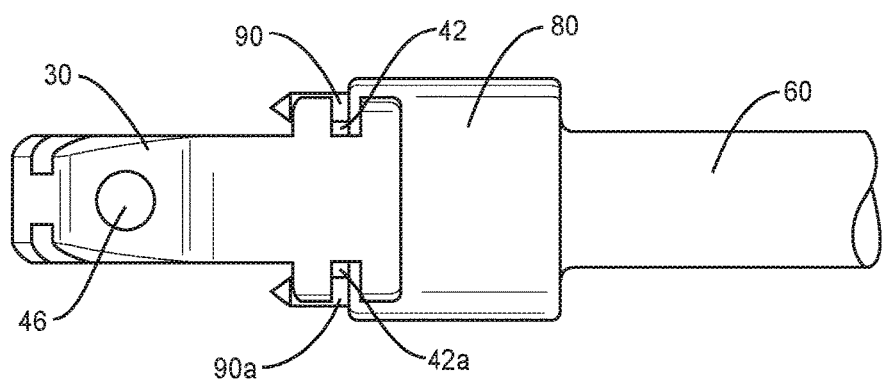
FIG. 4 is a side view of the components shown in FIG. 3.
Figure 5:
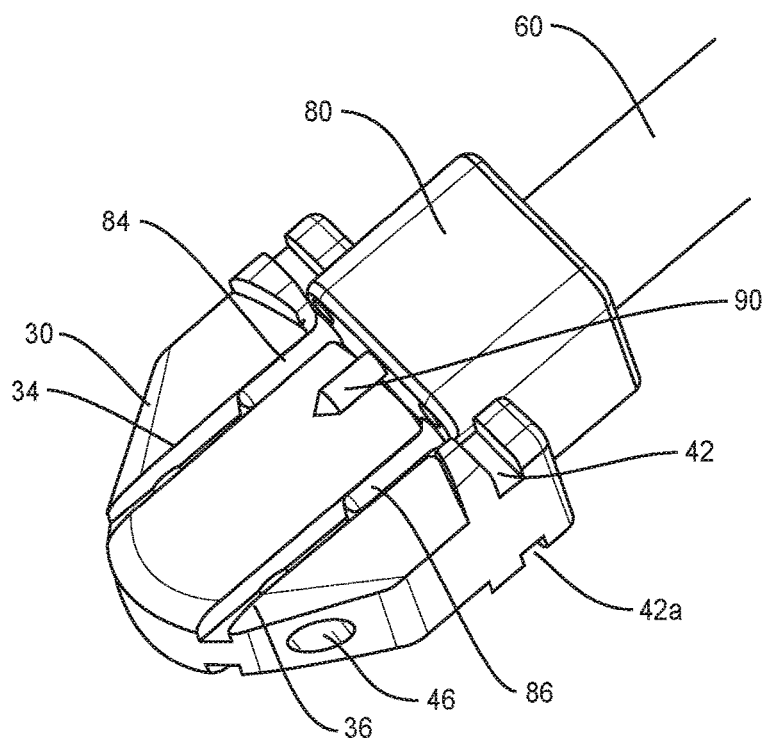
FIG. 5 is a perspective view of the components shown in FIG. 3.
Figure 6:
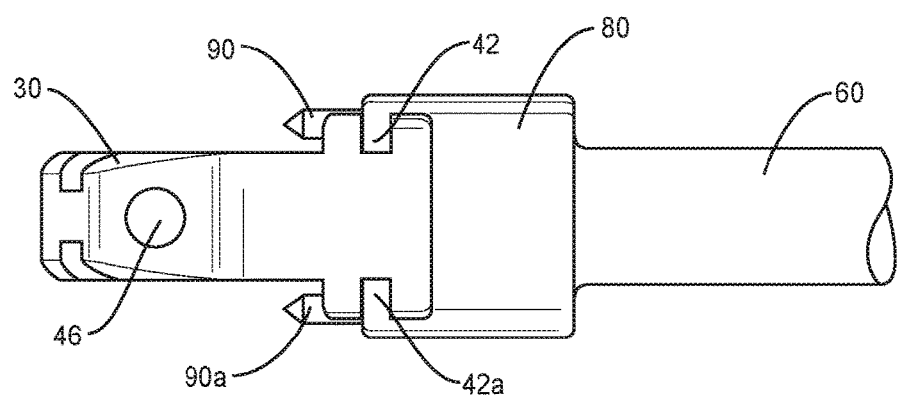
FIG. 6 is a side view of the components shown in FIG. 3.
Figure 7:
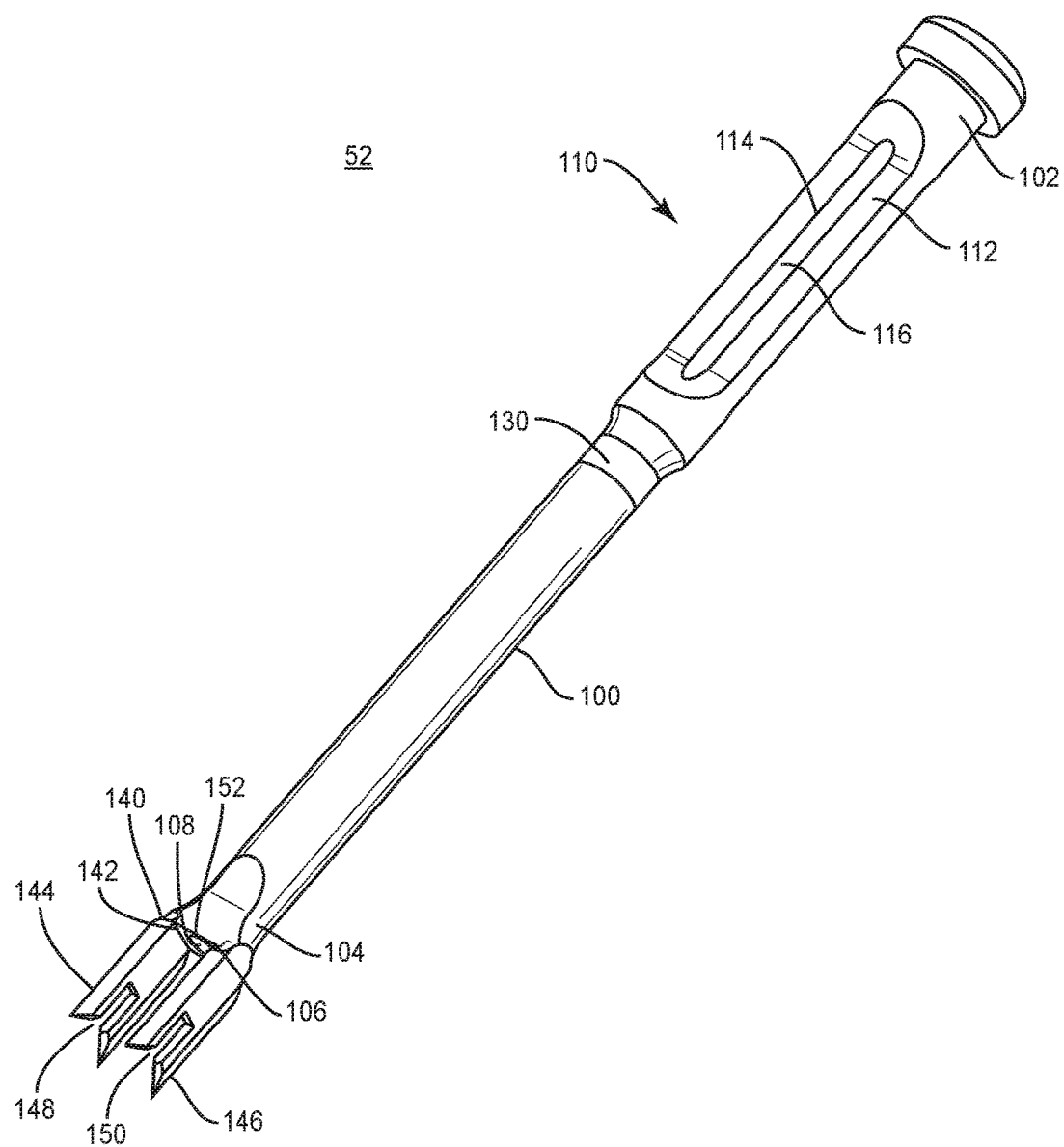
FIG. 7 is a perspective view of components of one embodiment of a surgical system in accordance with the principles of the present disclosure.

Slots 42, 42*a* are spaced apart and disposed on opposing sides of body 30, for example, corresponding to adjacent vertebral endplate surfaces. Slots 42, 42*a* are oriented to provide visual indicia of positioning of a surgical instrument, for example, drill guide 50 engaged with trial 12 between a spaced position, as shown in FIGS. 3 and 4, and a seated position, as shown in FIGS. 5 and 6. Slots 42, 42*a* are configured for disposal of a portion of drill guide 50 to facilitate a lateral view and/or verification of a spaced position and a seated position of a surgical instrument, for example, drill guide 50 relative to trial 12, as described herein.

In some embodiments, body 30 includes a surface 44 that defines an opening 46. In some embodiments, opening 46 includes a profile, such as, for example, a circular profile. In some embodiments, opening 46 may have various profile configurations, such as, for example, cylindrical, square, oval, rectangular, polygonal, irregular, tapered, offset, staggered and uniform. In some embodiments, surface 44 includes radiomarkers for identification of orientation of trial 12 under x-ray, fluoroscopy, CT or other imaging techniques. In some embodiments, opening 46 is configured to indicate orientation and positioning of trial 12 with tissue, and/or orientation and positioning, for example, seating of trial 12 with a surgical instrument. In some embodiments, as trial 12 is positioned between adjacent vertebrae, opening 46 is viewed under x-ray, fluoroscopy, CT or other imaging techniques to confirm that trial 12 is properly oriented. As body 30 is manipulated, a view of the profile of opening 46 changes, for example, the profile is a half moon shape. When body 30 is properly oriented, the profile of opening 46 is viewed in full, for example, a full circle.

Drill guide 50 includes a shaft 60 that extends between an end 62 and an end 64 and defines an axis X2. Shaft 60 includes a surface 66 that defines an opening, such as, for example, a passageway 68. Passageway 68 is configured for axial translation and/or rotation of handle 14 therein to facilitate alignment, engagement and disengagement of drill guide 50 with trial 12, as described herein. End 62 includes a handle 70 configured to facilitate manipulation of drill guide 50. Handle 70 includes opposing planar surfaces or flats to facilitate manipulation of drill guide 50. Handle 70 also includes opposing undulating surfaces to facilitate manipulation of drill guide 50.

Handle 70 includes a surface 72 that defines a plurality of openings 74. Openings 74 are equidistantly spaced apart about handle 70 for selective alignment with tissue, for example, with adjacent vertebrae. In some embodiments, openings 74 are configured for disposal of a portion of a drill, for example, to orient the drill with tissue of adjacent vertebrae, as described herein. In some embodiments, end 62 includes indicia, such as, for example, a band 76. In some embodiments, band 76 includes a color configured to match the color of band 22 of trial 12, for example, corresponding to a size and dimension of an implant, as described herein.

End 64 includes a body 80. Body 80 includes a surface 82 that defines a mating part, such as, for example, a fin 84 and a fin 86. Fin 84 and fin 86 are spaced apart and each extends axially along axis X2. Fins 84, 86 are slidably engageable with the surfaces of slots 34, 36 for axial translation of drill guide 50 relative to trial 12. This configuration facilitates removable, mating engagement of drill guide 50 with trial 12, as described herein. In some embodiments, fin 84 extends in alternate orientations relative to axis X2, such as, for example, transverse, perpendicular and/or other angular orientations such as acute or obtuse. In some embodiments, fin 86 extends axially along axis X2. In some embodiments, fin 86 extends in alternate orientations relative to axis X2, such as, for example, transverse, perpendicular and/or other angular orientations such as acute or obtuse. In some embodiments, the compatibility and/or interchangeability of slots 34, 36 with fins 84, 86 facilitates utilizing various surgical instruments with trial 12 during the surgical procedure while maintaining body 30 between adjacent vertebrae.

In some embodiments, surface 32 defines protrusions, such as, for example, pins 90, 90*a*. Pins 90, 90*a* extend along axis X2. Pins 90 are configured to engage adjacent vertebrae to stabilize drill guide 50 relative to the vertebrae and trial 12 while utilizing the alternate surgical instruments for engaging, cutting and/or otherwise treating tissue during a surgical procedure. Drill guide 50 is configured for translation relative to trial 12 between a spaced orientation, as shown in FIGS. 3 and 4, and a seated orientation, as shown in FIGS. 5 and 6. In the spaced orientation, pins 90, 90*a* are disposed with and visible within slots 42, 42*a*, and body 80 is spaced from body 30 such that body 80 is out of alignment with slots 42, 42*a*. As such, body 80 is not laterally visible in slots 42, 42*a*. In the seated orientation, pins 90, 90*a* are translated forward out of alignment with slots 42, 42*a*, and body 80 engages body 30 such that body 80 is disposed and in alignment with slots 42, 42*a*. As such, body 80 is laterally visible in slots 42, 42 to confirm positioning of drill guide 50 with trial 12 in a mated engagement.

Rail punch 52 includes a shaft 100 that extends between an end 102 and an end 104 and defines an axis X3. Shaft 100 includes a surface 106 that defines an opening, such as, for example, a passageway 108. Passageway 108 is configured for axial translation and/or rotation of handle 14 therein to facilitate engagement and disengagement of rail punch 52 with trial 12, as described herein. End 102 includes a handle 110 configured to facilitate manipulation of rail punch 52. In some embodiments, handle 110 includes a planar portion 112. Portion 112 includes a surface 114 that defines an elongate opening 116. Opening 116 provides access to handle 14 and/or knurled surface 24 to facilitate simultaneous manipulation and removal of trial 12 and rail punch 52. In some embodiments, end 102 includes indicia, such as, for example, a band 130. In some embodiments, band 130 includes a color configured to match the color of band 22 of trial 12, for example, corresponding to a size and dimension of an implant, as described herein.

Figure 8:
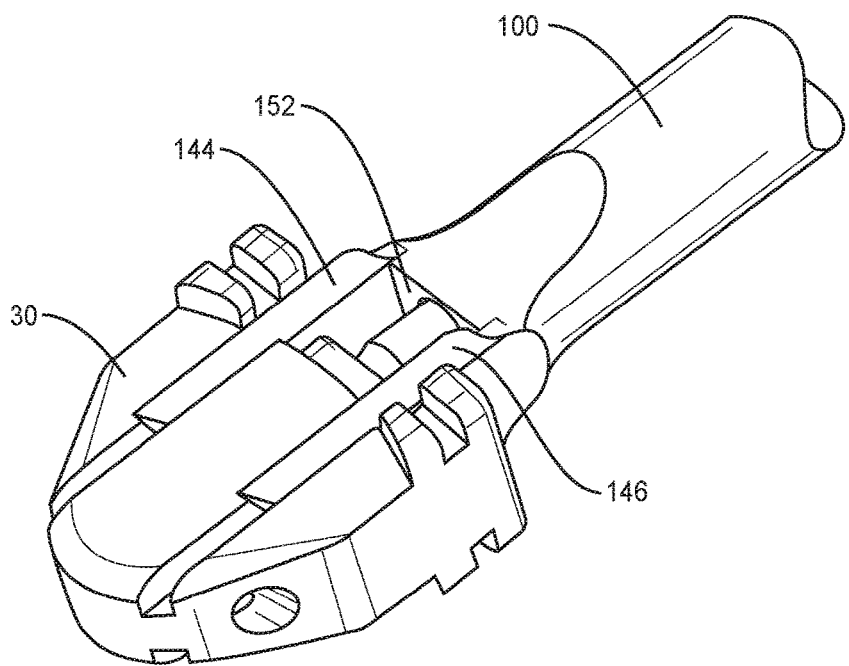
FIG. 8 is an enlarged break away view of components of one embodiment of a surgical system in accordance with the principles of the present disclosure.
Figure 9:
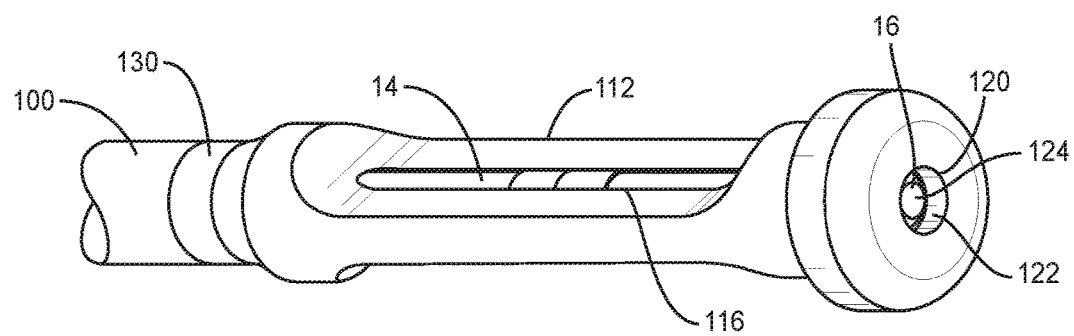
FIG. 9 is an enlarged break away view of the components shown in FIG. 7.
Figure 10:
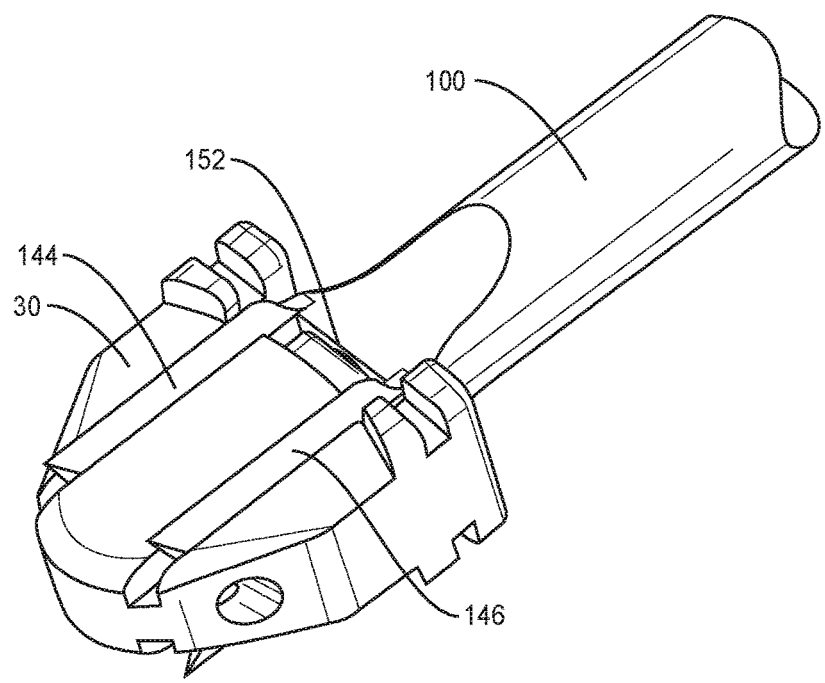
FIG. 10 is a perspective view of the components shown in FIG. 8.
Figure 11:
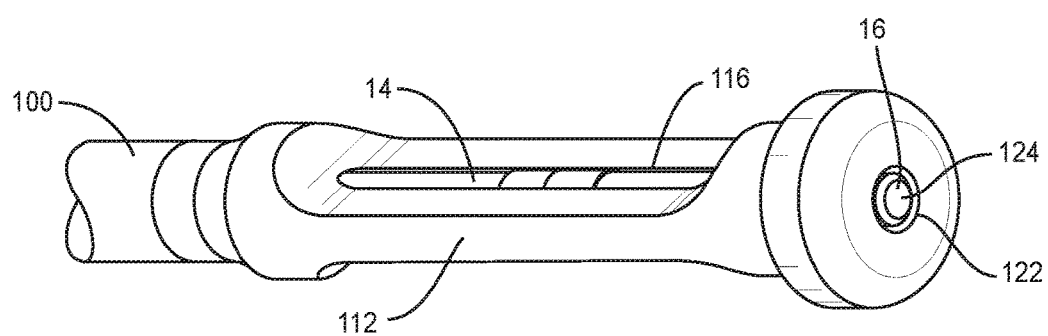
FIG. 11 is a perspective view of the components shown in FIG. 9.

End 102 includes a surface 120 that defines an opening 122. Opening 122 is configured for disposal of end 16 to indicate position of rail punch 52 relative to trial 12 between a spaced orientation, as shown in FIGS. 8 and 9, and a seated orientation, as shown in FIGS. 10 and 11. In the spaced orientation, a surface 124 of end 16 is disposed out of alignment and/or in a recessed orientation with surface 120. In the seated orientation, surface 124 of end 16 is aligned and disposed in an even, flush orientation with surface 120.

End 104 includes a body 140. Body 140 includes a surface 142 that defines a mating part, such as, for example, a fin that includes a cutting blade 144 and a fin that includes a cutting blade 146. Cutting blade 144 includes an opening 148 configured for disposal of trial 12. Cutting blade 146 includes an opening 150 configured for disposal of trial 12. The fins of body 140, which include cutting blades 144, 146, are disposed in a spaced apart relation to facilitate mating engagement with slots 34, 36. The fins of body 140 are slidably engageable with the surfaces of slots 34, 36 for axial translation of rail punch 52 relative to trial 12. This configuration facilitates removable, mating engagement of rail punch 52 with trial 12, as described herein. In some embodiments, the compatibility and/or interchangeability of slots 34, 36 with the fins of body 140 facilitates utilizing various surgical instruments with trial 12 during a surgical procedure while maintaining body 30 with vertebrae.

Cutting blade 144 and cutting blade 146 are spaced apart and each extends axially along axis X3. Cutting blades 144, 146 are aligned with slots 34, 36 and configured for engaging, cutting and/or otherwise treating tissue during a surgical procedure. In some embodiments, cutting blade 144 and/or cutting blade 146 include a taper, sharpened tip and/or angled cutting surface for engagement with tissue, for example, pilot holes. In some embodiments, cutting blade 144 and/or cutting blade 146 can extend in alternate orientations relative to axis X3, such as, for example, transverse, perpendicular and/or other angular orientations such as acute or obtuse. In some embodiments, surface 142 defines a stop surface 152. In some embodiments, surface 152 engages body 140 in the seated orientation of rail punch 52 with trial 12, and/or provides visual and/or tactile indicia of such engagement. In some embodiments, surface 152 is configured to resist and/or prevent cutting blades 144, 146 from engaging tissue beyond a selected depth.

Figure 12:
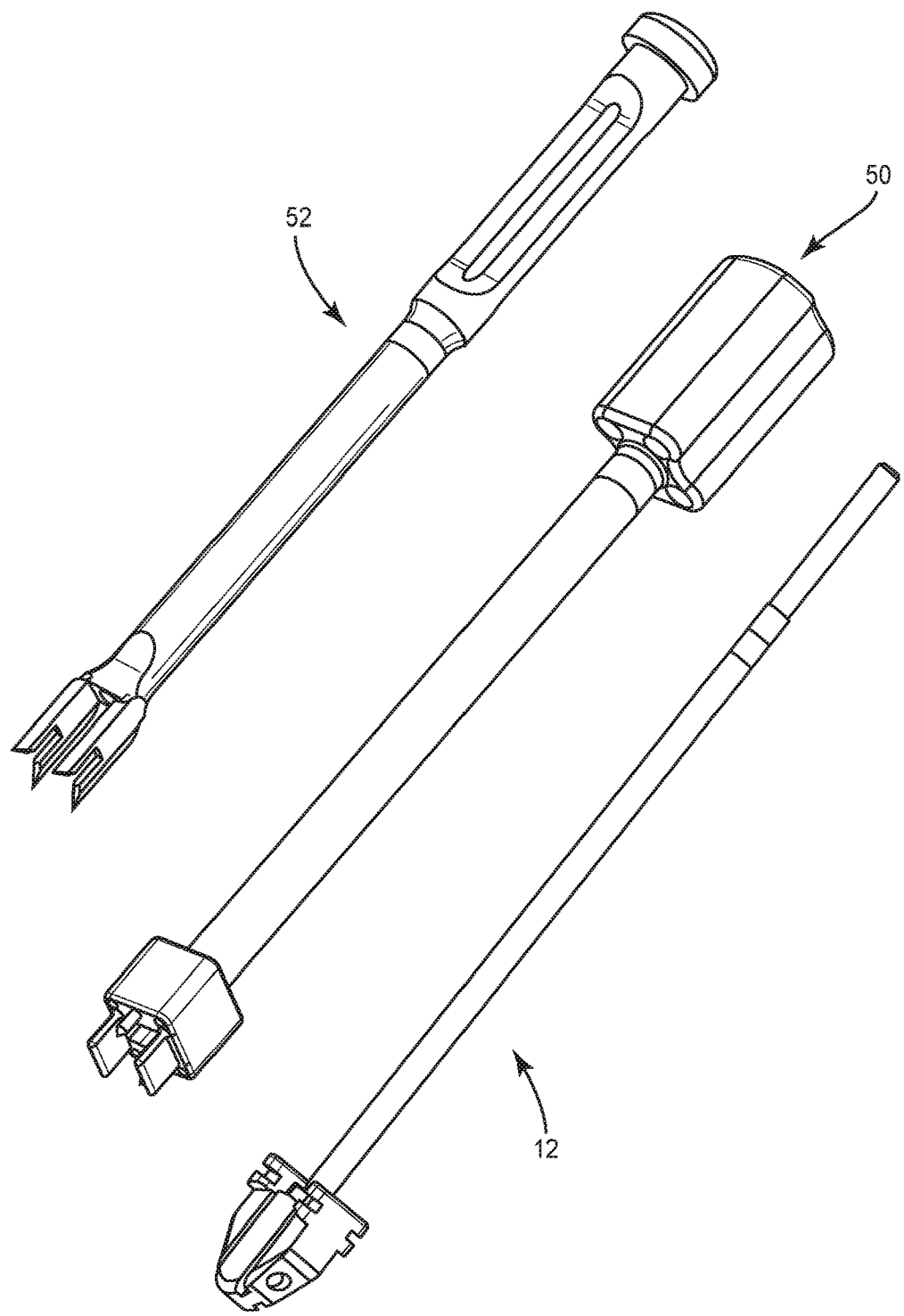
FIG. 12 is a perspective view of components of one embodiment of a surgical system in accordance with the principles of the present disclosure.

In assembly, operation and use, surgical system 10, similar to the systems and methods described herein, is provided as a kit including a trial 12 that is interchangeable and/or compatible with one or a plurality of alternate surgical instruments, such as, for example, a drill guide 50 and a rail punch 52, as described herein and shown in FIG. 12. Surgical system 10 is employed with a surgical procedure for treatment of a spinal disorder affecting a section of a spine of a patient, as discussed herein. For example, trial 12 can be used with a surgical procedure for treatment of a condition or injury of an affected section of the spine including vertebrae V, as shown in FIGS. 13-19. In some embodiments, one or more components of surgical system 10 can be delivered or implanted as a pre-assembled device, or can be assembled in vivo and/or in situ. In some embodiments, one or more components of surgical system 10 may be completely or partially revised, removed or replaced.

The components of surgical system 10 can be employed with a surgical treatment, for example, to replace all or a portion of an intervertebral disc in connection with a disc arthroplasty, which includes insertion of an artificial intervertebral disc implant 200 into an intervertebral space S between adjacent vertebrae V1, V2 for treating an applicable condition or injury of an affected section of a spinal column and adjacent areas within a body. In some embodiments, surgical system 10 may be employed with other surgical procedures, such as, for example, discectomy, laminotomy, laminectomy, nerve root retraction, foramenotomy, facetectomy, decompression, and spinal or nucleus replacement.

In some embodiments, the components of surgical system 10 may be employed with one or a plurality of vertebra. To treat a selected section of vertebrae V, a medical practitioner obtains access to a surgical site including vertebrae V in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area.

Figure 13:
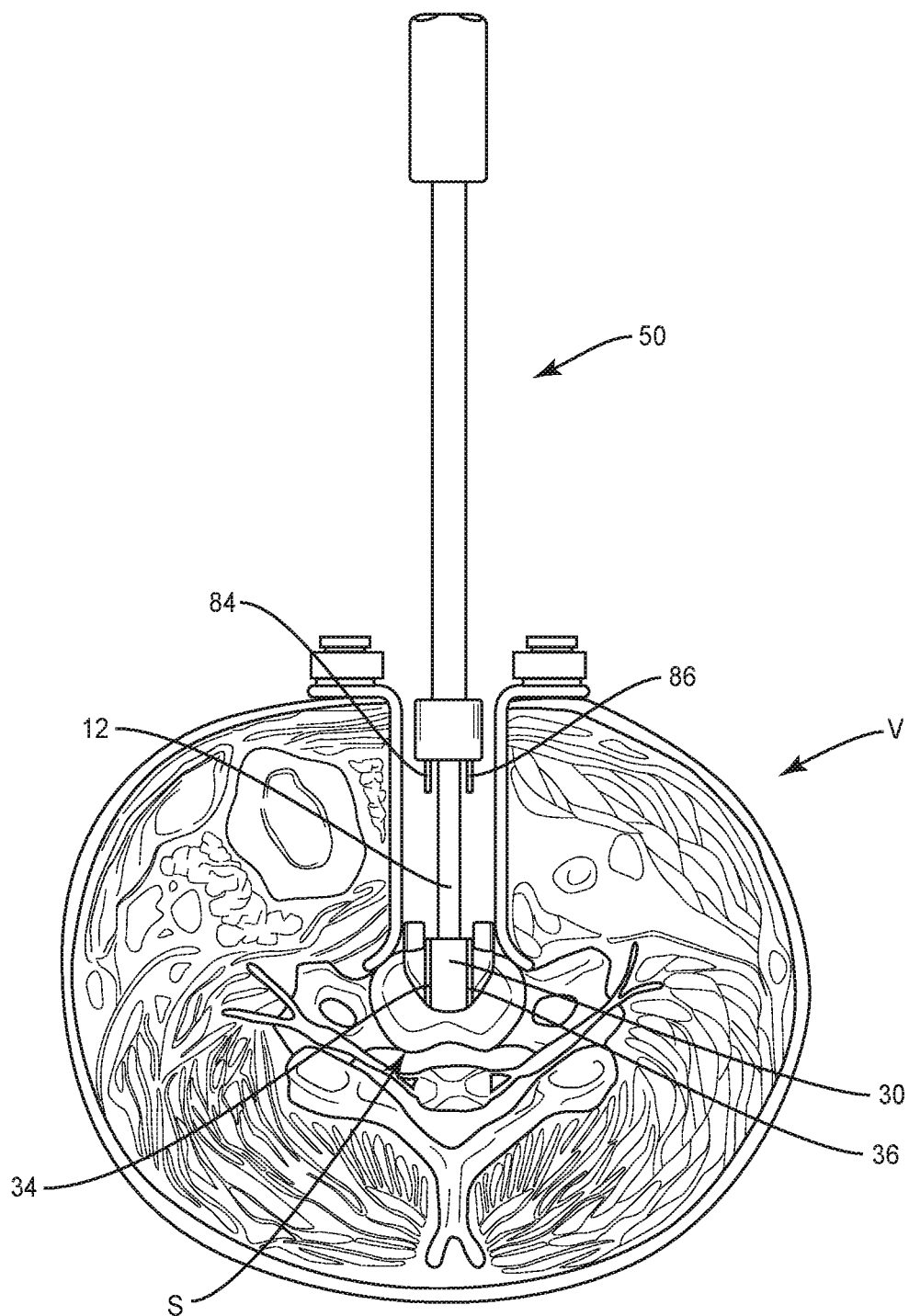
FIG. 13 is a plan view of components of one embodiment of a surgical system in accordance with the principles of the present disclosure disposed with vertebrae.

An incision is made in the body of a patient, as shown in FIG. 13, and a cutting instrument (not shown) creates a surgical pathway for delivery of components of surgical system 10 adjacent intervertebral space S. Once access to the surgical site is obtained, the surgical procedure can be performed for treating the spine disorder. In some embodiments, surgical system 10 can be used to provide support and stabilize vertebrae V. In some embodiments, components of surgical system 10 are employed to remove some or all of the disc tissue adjacent intervertebral space S including the disc nucleus and fluids, adjacent tissues and/or bone, which may include corticating, scraping and/or removing tissue from the surfaces of endplates E1, E2 of opposing vertebrae V1, V2, as well as for aspiration and irrigation of the region.

In some embodiments, after discectomy and decompression is completed, exterior distraction devices are removed. In some embodiments, a round or cylindrical burr is utilized to prepare endplates E1, E2 so that they are flat and parallel. In some embodiments, preparation of posterior areas of endplates E1, E2 of vertebrae V1, V2 is performed to facilitate implant interface with endplates E1, E2. In some embodiments, surgical system 10 includes a shim distractor to assist in the introduction of instruments into intervertebral space S, or during preparation endplates E1, E2, should intervertebral space S collapse without external distraction. In some embodiments, surgical system 10 includes a rasp with a burr for preparation of endplates E1, E2 to facilitate implant interface with endplates E1, E2.

Endplates E1, E2 are prepared and a size of trial 12 is determined. In some embodiments, trial 12 can be color coded for sizing, as described herein. In some embodiments, surgical system 10 includes a trial 12 that measures intervertebral space S height, depth, and width to facilitate engagement of implant 200 with endplates E1, E2. In some embodiments, engagement of trail 12 with endplates E1, E2 is snug without requiring further distraction. In some embodiments, surgical system 10 includes a device for tapping trial 12 into intervertebral space S and/or to determine if an alternately sized, for example, a smaller trial 12 may be required.

Trial 12 is inserted into intervertebral space S such that body 30 is engageable with endplates E1, E2. Positioning can be verified with fluoroscopy. Drill guide 50 is translated over handle 14, as described herein, to connect, attach, assemble and/or mate drill guide 50 with trial 12 for engaging, cutting and/or otherwise treating vertebrae V1, V2. Fins 84, 86 slidably engage the surfaces of slots 34, 36 for axial translation of drill guide 50 relative to trial 12 such that drill guide 50 is removably engaged with trial 12, as described herein.

Figure 14:
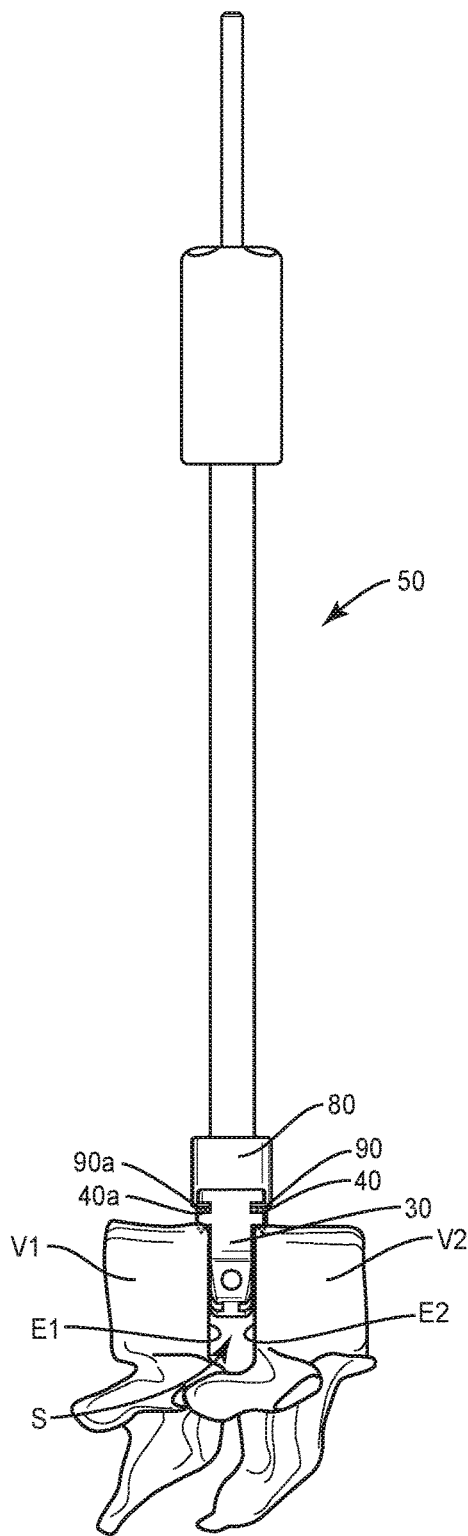
FIG. 14 is a side view of components of one embodiment of a surgical system in accordance with the principles of the present disclosure disposed with vertebrae.

Drill guide 50 is disposed in a spaced orientation, as described herein and shown in FIG. 14, such that pins 90, 90a are disposed with and visible within slots 42, 42a. Body 80 is spaced from body 30 such that body 80 is out of alignment with slots 42, 42a and not laterally visible in slots 42, 42a.

Figure 15:
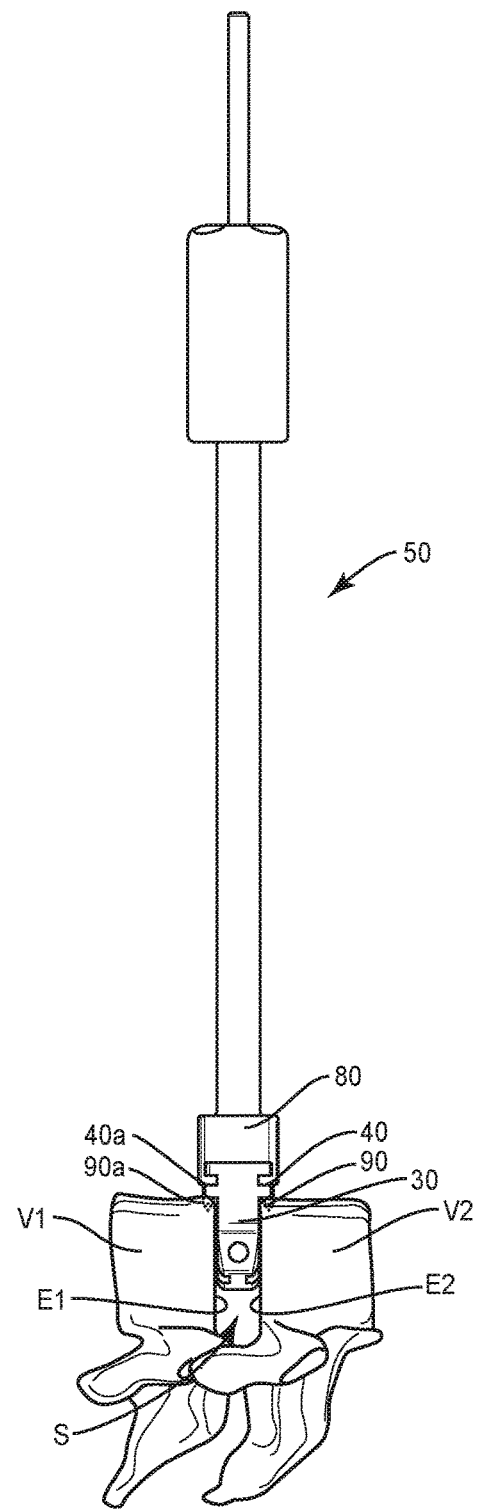
FIG. 15 is a side view of components of one embodiment of a surgical system in accordance with the principles of the present disclosure disposed with vertebrae.

Drill guide 50 is manipulated for disposal in a seated orientation, as described herein and shown in FIG. 15, such that pins 90, 90a are translated forward out of alignment with slots 42, 42a. Body 80 engages body 30 such that body 80 is disposed and in alignment with slots 42, 42a. Body 80 is laterally visible in slots 42, 42 to confirm positioning of drill guide 50 with trial 12 in a mated engagement.

Figure 16:
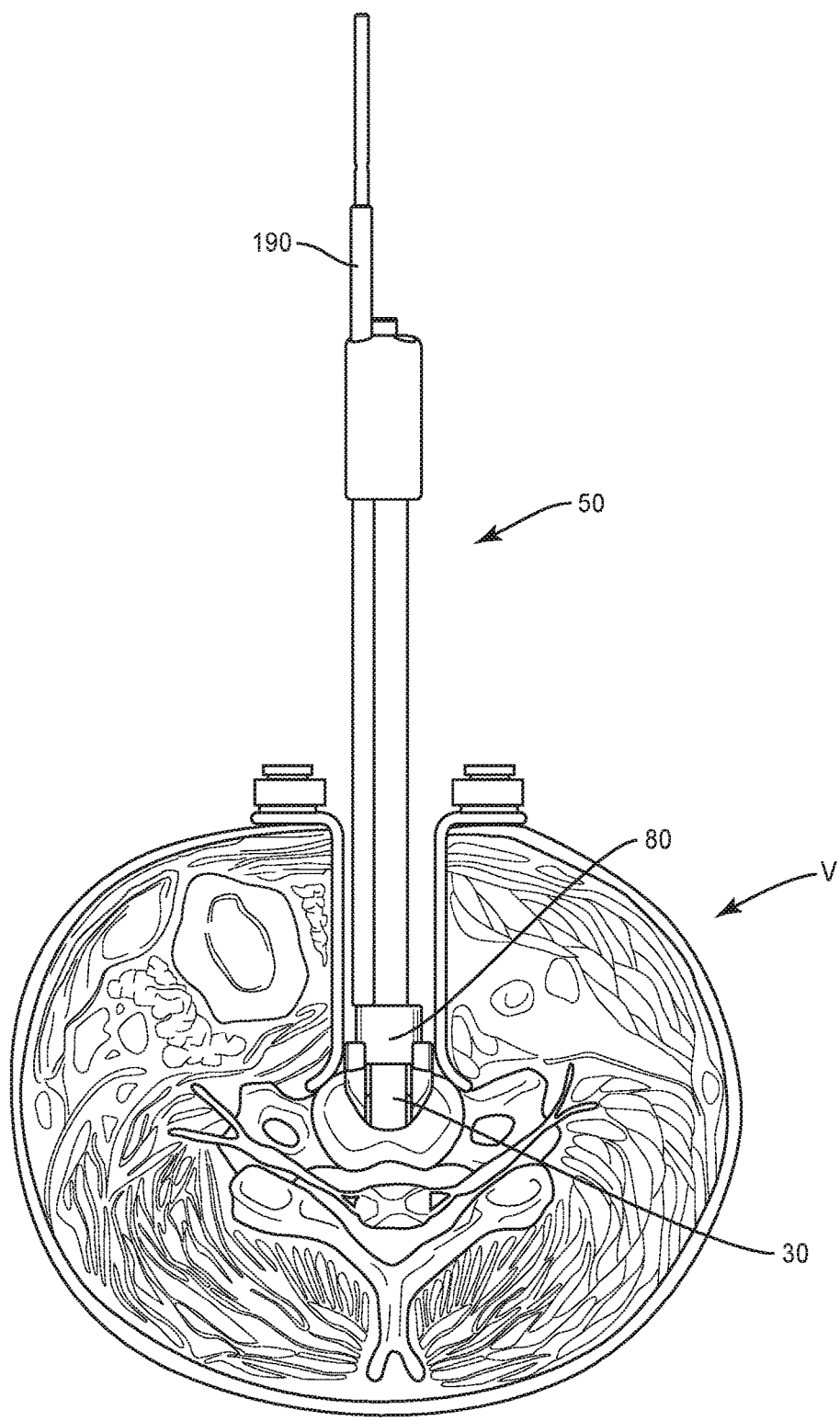
FIG. 16 is a plan view of components of one embodiment of a surgical system in accordance with the principles of the present disclosure disposed with vertebrae.

Pin 90a engages vertebra V1 and pin 90 engages vertebra V2 to stabilize drill guide 50 relative to vertebrae V and trial 12 during engagement and/or drilling of one or more pilot holes with the tissue of vertebrae V1, V2. Pilot holes are cut and/or drilled adjacent to endplate E1 of vertebra V1 and endplate E2 of vertebra V2. The pilot holes are created in the tissue in connection with preparation of fixation channels in endplates E1, E2 to facilitate engagement of rails of implant 200 with vertebrae V1, V2, as shown in FIG. 16.

A surgical instrument, such as, for example, a drill 190 is disposed with each of the openings of body 80, as described herein, to align a cutting surface of drill 190 with selected tissue of endplates E1, E2 to form the pilot holes in vertebrae V1, V2. A first pilot hole is cut into tissue of vertebra V1 adjacent endplate E1 and aligned with a corresponding opening of body 80, for example, an upper left or right opening of body 80. In some embodiments, a temporary fixation pin is disposed with the first hole to facilitate alignment of tissue with body 80. A second pilot hole, spaced apart from the first pilot hole, is cut into tissue of vertebra V1 adjacent endplate E1 and aligned with a corresponding opening of body 80. In some embodiments, a temporary fixation pin is disposed with the second hole to facilitate alignment of tissue with body 80. Third and fourth pilot holes are cut into tissue of vertebra V2 adjacent endplate E2, similar to the first and second pilot holes. In some embodiments, the temporary fixation pins are removed.

Drill guide 50 is manipulated for removal from trial 12. Handle 70 is manipulated such that fins 84, 86 slidably engage the surfaces of slots 34, 36 for axial translation of drill guide 50 relative to trial 12 such that drill guide 50 disengages from trial 12. Drill guide 50 is removed from intervertebral space S such that body 30 remains disposed with intervertebral space S between vertebrae V1, V2. Trial 12 remains disposed with intervertebral space S between vertebrae V1, V2 for engagement with one or more alternate surgical instruments, as described herein.

Rail punch 52 is translated over handle 14, as described herein, to connect, attach, assemble and/or mate rail punch 52 with trial 12 for engaging, cutting and/or otherwise treating vertebrae V1, V2. The fins of body 140, which include cutting blades 144, 146, slidably engage the surfaces of slots 34, 36 for axial translation of rail punch 52 relative to trial 12 such that rail punch 52 is removably engaged with trial 12, as described herein. Body 30 is disposed within openings 148, 150.

Figure 17:
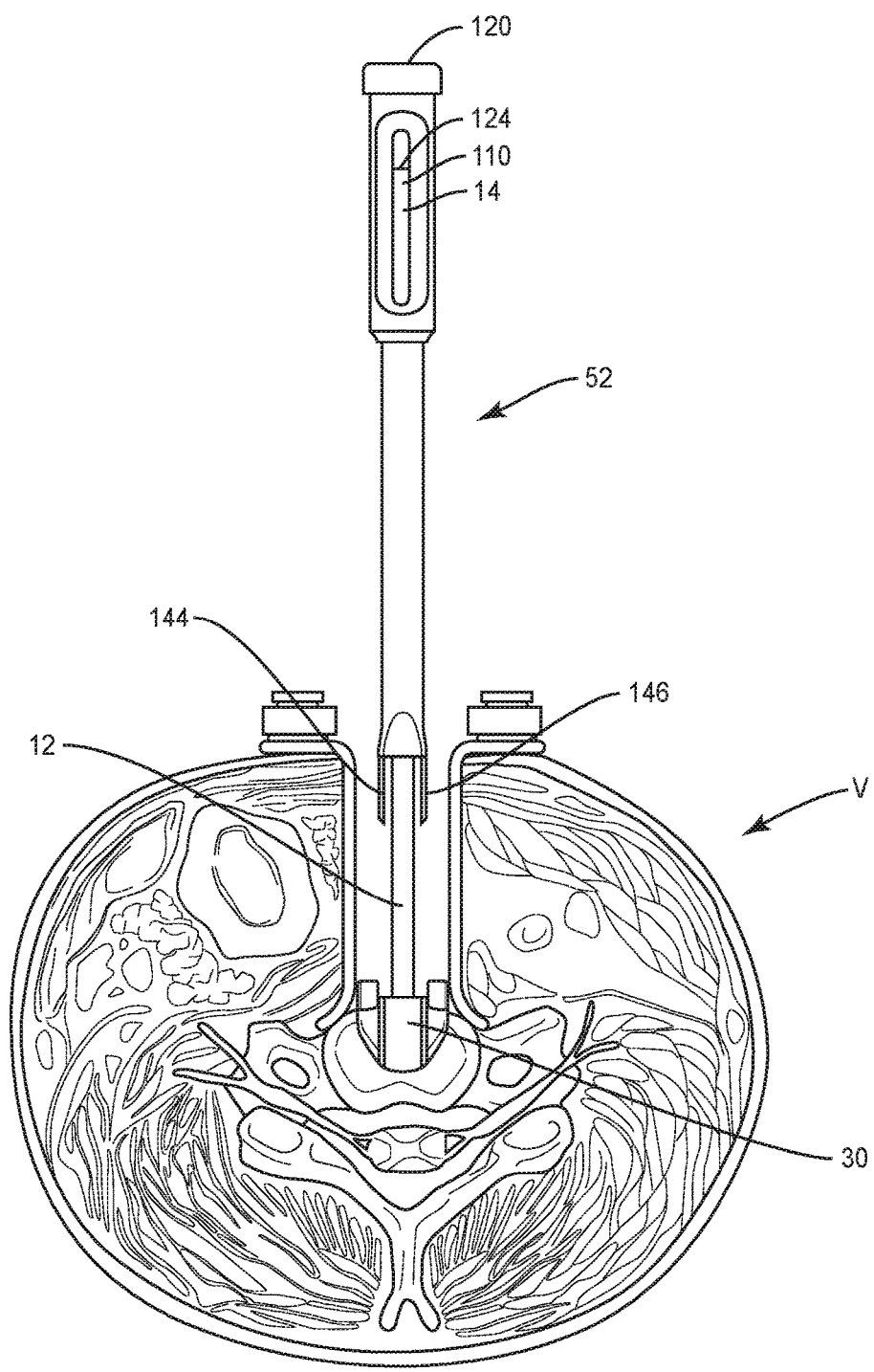
FIG. 17 is a plan view of components of one embodiment of a surgical system in accordance with the principles of the present disclosure disposed with vertebrae.
Figure 18:
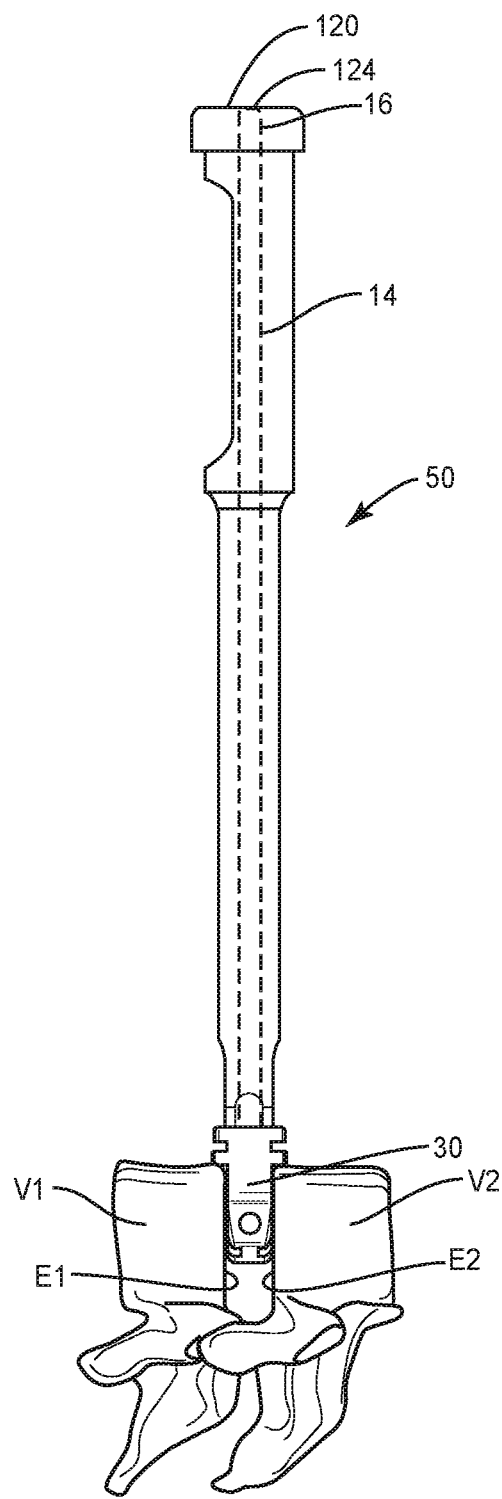
FIG. 18 is a side view of components of one embodiment of a surgical system in accordance with the principles of the present disclosure disposed with vertebrae.

Trial 12 is disposed with intervertebral space S between vertebrae V1, V2 and the fins of body 140 slide along slots 34, 36 such that cutting blades 144, 146 are aligned with the pilot holes formed in vertebrae V1, V2, described above using drill guide 50. Rail punch 52 is translated along trial 12 from a spaced orientation, as shown in FIG. 17, to a seated orientation, as shown in FIG. 18. As rail punch 52 translates along trial 12, blades 144, 146 engage and cut tissue adjacent the pilot holes to form channels at the pilot hole locations. The channels are formed in vertebrae V1, V2 adjacent endplates E1, E2 for disposal of projections 202 of implant 200, and facilitate implant interface and engagement with vertebrae V1, V2. Positioning can be verified with fluoroscopy. In some embodiments, a mallet (not shown) is utilized to seat rail punch 52 with trial 12.

In some embodiments, in the seated orientation of rail punch 52 with trial 12, surface 124 of end 16 is aligned and disposed in an even, flush orientation with surface 120. In some embodiments, in the seated orientation of rail punch 52 with trial 12, surface 152 engages body 140, and/or provides visual and/or tactile indicia of such engagement. In some embodiments, opening 46 of body 30 indicates orientation and positioning of blades 144, 146 with trial 12 and/or vertebrae V1, V2, for example, the seated orientation of rail punch 52 with trial 12.

Rail punch 52 and trial 12 are manipulated for removal from intervertebral space S. Handle 110 and knurled surface 24 are manipulated simultaneously, as described herein, such that rail punch 52 and trial 12 are simultaneously removed from intervertebral space S. In some embodiments, rail punch 52 and trial 12 can be grasped simultaneously and removed from intervertebral space S in one motion or step.

Figure 19:
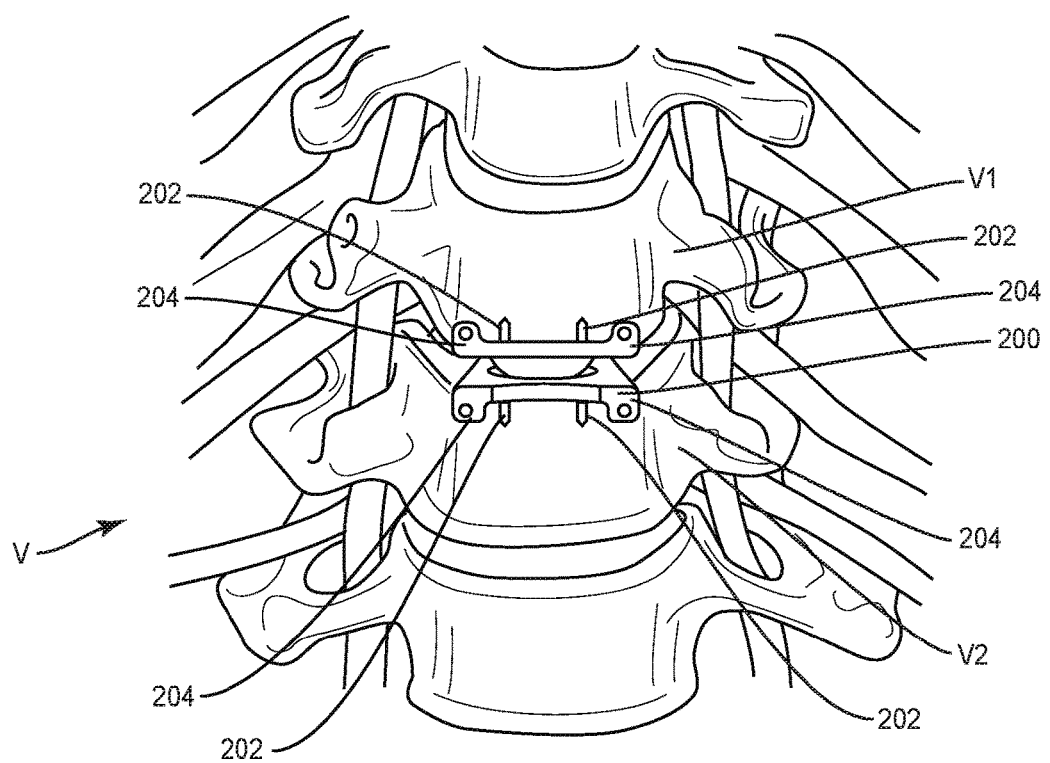
FIG. 19 is a plan view of components of one embodiment of a surgical system in accordance with the principles of the present disclosure disposed with vertebrae.

A surgical instrument, such as, for example, an inserter (not shown) is connected with a selected implant, for example, intervertebral disc implant 200. The inserter manipulates implant 200 such that projections 202 are aligned with the channels formed in vertebrae V1, V2 adjacent endplates E1, E2. Implant 200 is disposed with intervertebral space S between vertebrae V1, V2 for engagement with tissue in connection with the surgical procedure, as shown in FIG. 19. In some embodiments, implant 200 includes tabs 204 with openings configured for disposal of fasteners to facilitate fixation of implant 200 with vertebrae V1, V2.

Upon completion of the surgical procedure, the non-implanted components and assemblies of surgical system 10 are removed from the surgical site and the incision closed. In some embodiments, surgical instrument 12 is disassembled, as described herein, to facilitate cleaning of one or all of the components. Surgical instrument 12 may be re-assembled for use in a surgical procedure. In some embodiments, surgical system 10 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit.

In some embodiments, surgical system 10 may include one or a plurality of plates, connectors, spinal rods and/or bone fasteners for use with a single vertebral level or a plurality of vertebral levels. In some embodiments, surgical system 10 may include fastening elements configured for fixation with vertebrae to secure joint surfaces and components, and provide complementary stabilization and immobilization to a vertebral region.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of fixation elements with vertebrae V. The components of surgical system 10 can be made of radiolucent materials such as polymers. Radio-markers may be included for identification under x-ray, fluoroscopy, CT or other imaging techniques, as described herein. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a trial including a shaft that extends along a longitudinal axis between opposite first and second ends, the second end including a body, the body comprising opposite first and second surfaces that each extend from a first end surface of the body to an opposite second end surface of the body, the first surface including a ledge positioned between the end surfaces, the body comprising first and second slots that extend into the first surface and third and fourth slots that extend into the second surface, the first and second surfaces being fixed relative to one another, the first and third slots extending parallel to the longitudinal axis and the second and fourth slots extending transverse to the longitudinal axis, the first slot having a total length that extends from the ledge to the second end surface, the second slot being positioned between the ledge and the first end surface; and
a member comprising a body having a tissue engagement surface, the member comprising a pair of fins that are slidably engageable with the first and third slots such that the trial is interchangeable with a plurality of alternate members,
wherein the member is configured for translation between a spaced orientation in which the body of the member is not visible within the second and fourth slots and a seated orientation in which the body of the member is visible within the second and fourth slots.

2. A surgical instrument as recited in claim 1, wherein the trial includes an elongated handle having a gripping surface.

3. A surgical instrument as recited in claim 1, wherein the trial includes a radiographic marker to identify a position of the trial.

4. A surgical instrument as recited in claim 1, wherein a distal end of the member includes at least one stability pin engageable with the trial.

5. A surgical instrument as recited in claim 1, wherein the member includes a depth stop engageable with the trial.

6. A surgical instrument as recited in claim 1, wherein the trial includes a handle and the member includes a handle, the handles including respective proximal surfaces aligned to verify mating engagement.

7. A surgical instrument as recited in claim 1, wherein the member includes a plurality of axially oriented openings alignable with tissue.

8. A surgical instrument as recited in claim 1, wherein the fins are axially oriented cutting blades.

9. A surgical instrument as recited in claim 1, wherein the first slot includes a pair of spaced apart slots and the third slot includes a pair of spaced apart slots.

10. A surgical instrument as recited in claim 1, wherein the first slot extends into the first surface without extending into the second surface and the third slot extends into the second surface without extending into the first surface.

11. A surgical instrument as recited in claim 1, wherein the second slot extends into the first surface without extending into the second surface and the fourth slot extends into the second surface without extending into the first surface.

12. A surgical instrument as recited in claim 1, wherein the first slot is positioned opposite the third slot.

13. A surgical instrument as recited in claim 1, wherein the first slot includes a pair of spaced apart slots and a distal end of the member includes a stability pin that is positioned between the pair of spaced apart slots when the member is in the seated orientation.

14. A surgical instrument as recited in claim 1, wherein the first slot includes a pair of spaced apart first slots, the third slot includes a pair of spaced apart third slots, and a distal end of the member includes a first stability pin that is positioned between the pair of spaced apart first slots when the member is in the seated orientation and a second stability pin that is positioned between the pair of spaced apart third slots when the member is in the seated orientation.

15. A surgical instrument as recited in claim 1, wherein the fins extend from the body of the member in a cantilevered configuration.

16. A surgical instrument as recited in claim 1, wherein the fins are spaced apart from one another.

17. A surgical instrument as recited in claim 1, wherein the member includes a shaft and a passageway that extends through the shaft and the body of the member, the passageway being configured for insertion of the shaft of the trial.

18. A surgical instrument as recited in claim 1, wherein the member includes a shaft defining a passageway, the body of the member being coupled to a distal end of the shaft, the body of the member comprising an opening that extends through a distal end surface of the body of the member, the opening being in communication with the passageway such that the shaft of the trial can be inserted through the opening and into the passageway.

19. A surgical system comprising:
a surgical instrument including a trial and a member being engageable with adjacent vertebral surfaces, the trial including a shaft that extends along a longitudinal axis between opposite first and second ends, the shaft being movably disposed in a shaft of the member such that the shafts are coaxial, the second end including a body that is permanently fixed relative to the shaft of the trial, the body comprising opposite first and second surfaces that each extend from a first end surface of the body to an opposite second end surface of the body, the first surface including a ledge positioned between the end surfaces, first and second slots that extend into the first surface and third and fourth slots that extend into the second surface, the first and second surfaces being connected by a wall such that the first and second surfaces are fixed relative to one another, the first and third slots extending parallel to the longitudinal axis and the second and fourth slots extending transverse to the longitudinal axis, the first slot having a total length that extends from the ledge to the second end surface, the second slot being positioned between the ledge and the first end surface, the member comprising a pair of fins that are slidably engageable with the first and third slots such that the trial is interchangeable with a plurality of alternate members; and a spinal implant disposable with the adjacent vertebral surfaces, wherein the member is configured for translation between a spaced orientation in which a body of the member is not visible within the second and fourth slots and a seated orientation in which the body of the member is visible within the second and fourth slots.

20. A surgical system as recited in claim 19, wherein the plurality of alternate members includes at least a tissue cutting guide and a tissue punch.

* * * * *